United States Patent [19]

Robinson et al.

[11] 4,352,922

[45] Oct. 5, 1982

[54] METHOD OF PRODUCING AN IMPROVED POLY-(AMIDE-IMIDE) RESIN BY REACTING A PHENANTHRENE WITH FORMALDEHYDE FOLLOWED BY OXIDIZING TO PRODUCE A POLYCARBOXYLATED PRODUCT FOLLOWED BY REACTION WITH AN AROMATIC DIAMINE

[75] Inventors: Joseph G. Robinson, Winchcombe; Angela M. Carswell, Longhope; David I. Barnes, Cheltenham, all of England

[73] Assignee: Coal Industry (Patents) Limited, London, England

[21] Appl. No.: 240,025

[22] Filed: Mar. 3, 1981

[30] Foreign Application Priority Data

Mar. 19, 1980 [GB] United Kingdom ................. 8009254

[51] Int. Cl.$^3$ .............................................. C08G 69/26
[52] U.S. Cl. ..................................... 528/232; 528/238; 528/242; 528/247; 528/266
[58] Field of Search ................ 528/232, 238, 242, 247, 528/266

[56] References Cited

U.S. PATENT DOCUMENTS 2,597,159 5/1952 May et al. ............................ 528/247
3,378,466 4/1968 Coltharp et al. ...................... 528/247

OTHER PUBLICATIONS

Chemical Abstract, vol. 76, 1972, pp. 18 and 19.

Organische Chemie, L. F. Fieser, et al., 1965, p. 1364.

Primary Examiner—Maurice J. Welsh
Attorney, Agent, or Firm—Stevens, Davis, Miller & Mosher

[57] ABSTRACT

According to the present invention, there is provided an improved method of producing a poly-(amide-imide) resin comprising the steps of:

(1) reacting a phenanthrene with formaldehyde or a formaldehyde donor in the presence of an acid catalyst to give a phenanthreneformaldehyde reaction product having substantially only methylene bridges;

(2) removing from the reaction product unreacted phenanthrene;

(3) treating the reaction product with formaldehyde or a formaldehyde donor in the presence of an acid catalyst to give a high molecular weight product having substantially only methylene bridges;

(4) oxidizing the high molecular weight product to break the 9, 10 bond in the phenanthrene moieties to produce a polycarboxylated reaction product;

(5) reacting the polycarboxylated reaction product with an aromatic diamine to produce a poly-(amide-imide) resin.

The resin would find use as a lamp capping cement, as a high temperature insulator, in copper clad high temperature printed circuits, in electrical heater panels, in transformers and in glass or asbestos laminates for use as compressor blades.

8 Claims, 1 Drawing Figure

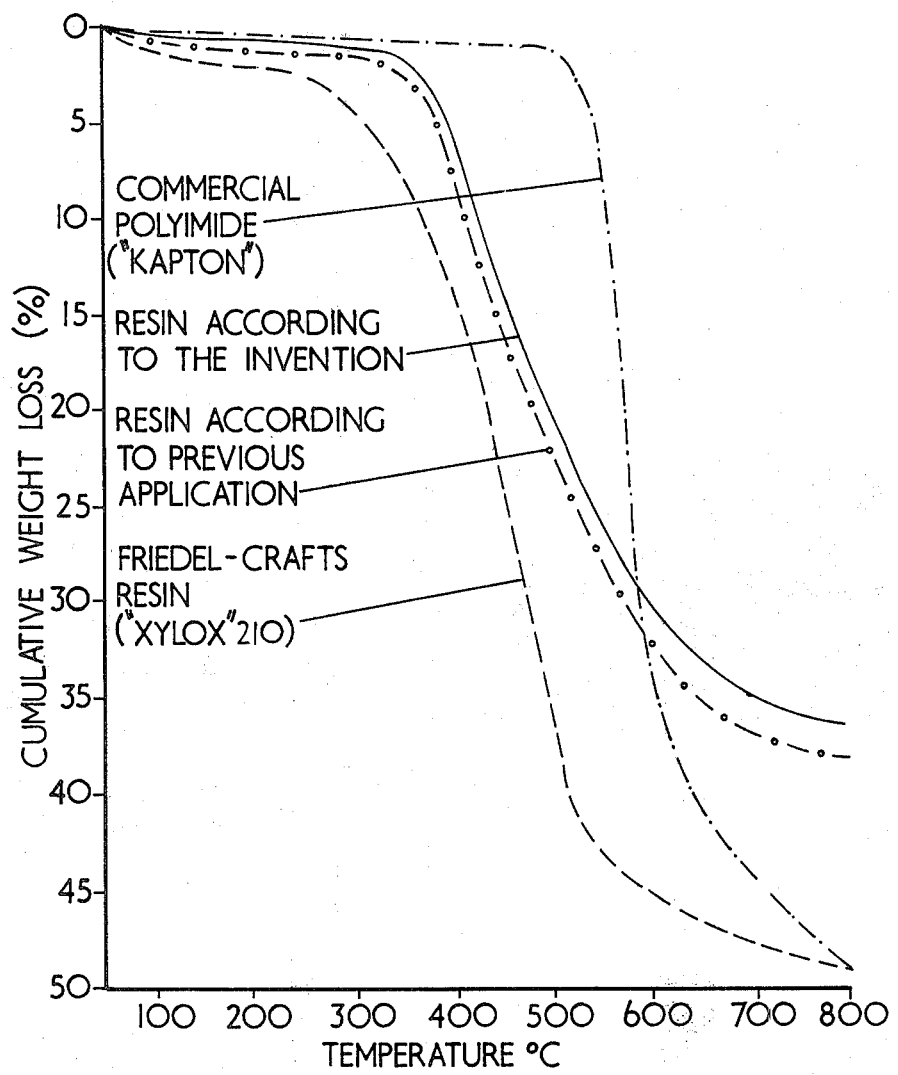

METHOD OF PRODUCING AN IMPROVED POLY-(AMIDE-IMIDE) RESIN BY REACTING A PHENANTHRENE WITH FORMALDEHYDE FOLLOWED BY OXIDIZING TO PRODUCE A POLYCARBOXYLATED PRODUCT FOLLOWED BY REACTION WITH AN AROMATIC DIAMINE

This invention relates to an improved poly-(amide-imide) resin, a process for its preparation and its use as a temperature resistant resin. In particular, but not exclusively, the invention relates to such a resin produced from cheaply available materials.

Several resins have been developed which are stable at high temperatures (in the region from 200° to 250° C. and even higher) and which retain their mechanical properties at these temperatures. These resins include polyimides, poly-(amide-imides), polybenzimidazoles, and polyphenylenes. These resins, apart from being derived from expensive materials, are very difficult to make. They have limited commercial acceptability either because of their high cost or because their chemical or physical properties are not adequate for their intended use. There are also resins made by Friedel-Crafts-type reactions which are cheaper but are less thermally stable than those mentioned above.

Another disadvantage of presently known resins is that they are made from petrochemicals. As the supply of petrochemicals is limited and rapidly decreasing the cost of these resins will therefore increase, and eventually they will be prohibitively expensive for most applications.

There is therefore a need for a thermally stable resin which is relatively cheap, which is made from readily available materials and which has good mechanical and physical properties. The resin would find use as a lamp capping cement, as a high temperature insulator, in copper clad high temperature printed circuits, in electrical heater panels, in transformers and in glass or asbestos laminates for use as compressor blades.

In our co-pending British Published Application No. 2,064,564 of June 17, 1982 we describe a method of producing a relatively cheap thermally stable resin from phenanthrene, alkylated phenanthrenes or mixtures thereof. The application describes a method of producing a phenanthrene-derived poly-(amide-imide) resin comprising the steps of:

(a) reacting a phenanthrene with formaldehyde or formaldehyde donor in the presence of an acid catalyst to give a phenanthrene-formaldehyde reaction product having substantially only methylene bridges joining the phenanthrene nuclei;

(b) oxidizing the reaction product to break the 9, 10 bond in the phenanthrene moieties to produce a polycarboxylated reaction product;

(c) reacting the polycarboxylated reaction product with an aromatic diamine to produce a poly-(amide-imide) resin.

The application also describes the basic chemistry of phenanthrene-derived poly-(amide-imide) resins and it is therefore incorporated herein by reference.

Although this method produces an acceptable poly-(amide-imide) resin with adequate thermal stability, the resin does not have very good impact resistance, tensile strength or elongation properties and cannot be drawn as long fibres. It is thought that the deficiences in the physical properties of the resin are due to the low molecular weight of the phenanthrene/formaldehyde reaction product and the presence therein of many oligomers of phenanthrene having terminal moieties linked to the chain at either the 9 or 10 position. On oxidation, such a reaction product will give rise to diphenic acid residues which will act as chain terminators on reaction with the aromatic diamine.

It is an object of the present invention to provide an improved method of producing a thermally stable resin having improved physical properties from phenanthrene.

There, according to the present invention, there is provided an improved method of producing a poly-(amide-imide) resin comprising the steps of:

(1) reacting a phenanthrene with formaldehyde or a formaldehyde donor in the presence of an acid catalyst to give a phenanthrene-formaldehyde reaction product having substantially only methylene bridges;

(2) removing from the reaction product unreacted phenanthrene;

(3) treating the reaction product with formaldehyde or a formaldehyde donor in the presence of an acid catalyst to give a high molecular weight product having substantially only methylene bridges;

(4) oxidizing the high molecular weight product to break the 9, 10 bond in the phenanthrene moieties to produce a polycarboxylated reaction product;

(5) reacting the polycarboxylated reaction product with an aromatic diamine to produce a poly-(amide-imide) resin.

The phenanthrene may be pure, or may contain alkylated derivatives. Phenanthrene may be readily isolated from the products of coal liquefaction and/or coal carbonization. This feedstock will remain in plentiful supply for as long as coal stocks last.

The formaldehyde, which is used in steps 1 and 3 may be formaldehyde itself, trioxane (a trimer of formaldehyde), formalin (38% formaldehyde in water) or, preferably, paraform, a solid polymer of formaldehyde and water containing about 87% formaldehyde.

The acid catalyst which is used in steps 1 and 3 may be independently protonic, such as hydrochloric acid or para-toluene sulphonic acid, or a Lewis acid, such as aluminium chloride, and is preferably sulphuric acid, advantageously having a concentration of about 50% in water.

To ensure that substantially only methylene bridges are obtained in the first step, it is preferred that the molar ratio of phenanthrene to formaldehyde is about 1 to 1 and that of phenanthrene to acid catalyst is about 1 to 2.

Preferably, the reaction of phenanthrene with formaldehyde is carried out in glacial acetic acid as the solvent. The glacial acetic does not dissolve the reaction product which therefore appears as an easily collectable precipitate.

Alternatively, the first step may be carried out in a solvent which dissolves both phenanthrene and the reaction product. The solvent is removed after the reaction and unreacted phenanthrene is removed by selective dissolution in a suitable solvent.

To ensure that substantially only methylene bridges are obtained in the third step it is preferred that the molar ratio of reaction product to formaldehyde is about 1 to 10. The high ratio of formaldehyde is needed to ensure that there is adequate reaction of the reaction product with the formaldehyde.

Preferably, the high molecular weight product is oxidizing by use of a peroxy organic acid, such as peroxy-acetic acid. Conveniently, the oxidation is carried out in an ether-like solvent such as dimethoxyethane. The oxidation step will also oxidize the methylene bridges to keto groups. This adds to the thermal stability of the resin as the keto groups deactive the rings to electrophilic attack by oxidizing agents.

The polycarboxlated reaction product contains many adjacent carboxyl groups and it is desirable that some, at least, of the adjacent carboxyl groups are dehydrated to form carboxylic acid anhydrides, for instance by treatment with acetic anhydride.

The polycarboxylated resin or its dehydrated derivative is then reacted with an aromatic diamine, such as 1-4-diamino benzene. Since there will be in the polycarboxylated reaction product some carboxyl groups that are not adjacent other carboxyl groups and which therefore cannot be converted into intra-anhydrides, the final product will contain both amide and imide linkages and will thus be a poly-(amide-imide) resin.

The method of the present invention is thought to be an improvement over the method described in our above mentioned application for the following reasons, although the invention is not to be limited to this explanation.

In the previous method, the reaction step (a) produces a phenanthrene formaldehyde resin having at its ends a proportion of phenanthrene moieties joined to the adjacent phenanthrene molecule by either its 9 or 10 position. On oxidation of this resin, the terminal 9- or 10-joined phenanthrene moieties will produce diphenic acid which will act as a chain stopper.

In the improved method of the present invention it is thought that after the removal of unreacted phenanthrene, the terminal molecules connected by their 9 or 10 positions are able to react with other reaction products through the agency of the formaldehyde at their 2 or 3 positions, the 10- or 9-position respectively being sterically hindered. This reaction has the effect that it increases the molecular weight of the reaction product and as such ensures that there is a minimum amount of diphenic acid formed on oxidation of the high molecular weight product. Thus there is considerably less chain stopper present that there would otherwise be, thereby allowing the poly-(amide-imide) resin to build up chains of greater length. This improves the physical properties of the resin. The thermal stability of the resin will be increased, but not by a great deal, because there will still be a proportion of amide linkages which are less thermally stable than the imide linkages. However, the proportion of amide linkages will be less than in the resin disclosed in our above mentioned application, and so that the improved resin will have somewhat higher thermal stability.

According to a second aspect of the present invention there is provided an improved poly-(amide-imide) resin made according to the method of the first aspect of the invention.

The invention also includes the high molecular weight product, its method of preparation, its oxidized derivative and varnishes including poly-(amide-imide) resins according to the invention.

The invention will now be described, by way of example only, with reference to the accompanying drawing, which shows a graph illustrating the thermal stability of various resins as determined by thermogravimetric analysis.

An improved poly-(amide-imide) resin was prepared as follows:

69 g (2 moles) of paraformaldehyde and 357 g (2.0 moles) of 56% w/w sulphuric acid were placed in a flanged flask fitted with a stirrer, condenser and thermometer and supported in an oil bath. As soon as the paraformaldehyde had dissolved, the temperature of the solution was raised to 100° C. and a charge of 178 g (1 mole) of phenanthrene was added to the flask. The reaction was allowed to continue for four hours, and thereafter 600 ml of 1,2-dichloroethane was added to dissolve the reaction product and unreacted phenanthrene. The reaction product solution was washed to neutrality with sodium carbonate solution and finally with water, and the solvent was distilled off in a rotary evaporator. The dried reaction product was stirred for at least one hour in four successive aliquots of 200 ml of glacial acetic acid at 100° C. The unreacted phenanthrene dissolved in the glacial acetic acid, which was discarded, leaving the reaction product as solid resin.

900 g of trioxane (a trimer of formaldehyde), 191 g of the reaction product, containing less than 5% of free phenanthrene, and 0.5% of toluene p-sulphonic acid (based on the weight of the resin reaction product) were heated with stirring at 135° C. for 1 hour to produce a high molecular weight product which was dissolved in 1,2-dichloroethane and the solution thereafter was filtered. The filtrate was washed with water to remove the acid, after which the solvent was removed by distillation in a rotary evaporator.

15 g of the high molecular weight product was dissolved in 1500 g 1,2-dichloroethane at 80° C. 360 g of a 40% solution of peracetic acid in glacial acetic acid was added to this solution and the mixture was allowed to reflux for four hours. The mixture was then poured into 2 liters of water to decompose the peracetic acid. The polycarboxylated product precipitated out, was isolated by decantation and adhering solvent was removed by distillation. The polycarboxylated product was dissolved in 20% sodium carbonate solution, and the carboxylic acid precipitated by the addition of 0.1 M hydrochloric acid to bring the pH of the solution to 1. The carboxylic acid was filtered off, washed to remove hydrochloric acid and dried in a vacuum desiccator.

15 g of the dry carboxylic acid product was dissolved in 200 ml of acetic anhydride and heated at 120° C. for 4 hrs to produce the anhydride of the carboxylic acid product.

The anhydride product (12 g) was dissolved in dimethyl sulphoxide (100 ml) and was added with stirring to a solution of 1,4 diamino benzene (10.81 g) in dimethyl sulphoxide (50 ml) to produce amide linkages. The resulting solution was poured onto a clear glass plate and heated in an oven for 3 hours, the temperature gradually being raised to a maximum of 300° C. at which it was maintained for the last hour. This produced a poly-(amide-imide) resin as a dark thin film.

Proton magnetic resonance spectrometry and infra spectrometry indicated the presence of both amide and imide linkages in the final resin.

The poly-(amide-imide) resin was subjected to thermogravimetric analysis in a nitrogen atmosphere. A commercial Friedel Crafts resin ("Xylok"-210), a commercial poly-imide resin ("Kapton") and a resin made according to the method of our previous application were also subjected to thermogravimetric analysis in a nitrogen atmosphere. The results of the analysis are shown in the drawing. It can be seen from this that the improved poly-(amide-imide) resin is less thermally stable than "Kapton" but more thermally stable than the "Xylok"-210 and the previous resin. It begins to decompose in the region of 400°–450° C. as compared to 500°–550° C. for "Kapton"; 250°–300° C. for "Xylok"-210 and 350°–400° C. for the previous resin.

The physical properties of the improved resin are compared with those of the previous resin in the following table.

TABLE.

| Property | Previous resin | Resin according to the invention |
| --- | --- | --- |
| Tensile strength | Fair | Good |
| Fiber forming ability | Fair | Good |

It is therefore clear that the improved poly-(amide-imide) will be useful as a heat resistant resin, and will be of commercial significance because it can be made by a simple process from cheaply available coal derived materials, and has adequate physical properties. "Kapton" and "Xylok"-210 are registered trade marks. All parts and percentages are by weight unless otherwise stated.

We claim:

1. An improved method of producing a poly-(amide-imide) resin comprising the steps of:
    (1) reacting a phenanthrene with formaldehyde or a formaldehyde donor in the presence of an acid catalyst to give a phenanthreneformaldehyde reaction product having substantially only methylene bridges;
    (2) removing from the reaction product unreacted phenanthrene;
    (3) treating the reaction product with formaldehyde or a formaldehyde donor in the presence of an acid catalyst to give a high molecular weight product having substantially only methylene bridges;
    (4) oxidizing the high molecular weight product to break the 9, 10 bond in the phenanthreme moieties to produce a polycarboxylated reaction product; and
    (5) reacting the polycarboxylated reaction product with an aromatic diamine to produce a poly-(amide-imide) resin.

2. A method according to claim 1, wherein the acid catalyst used in steps 1 and 3 is independently selected from the group consisting of hydrochloric acid, para-toluene sulphonic acid, sulphuric acid or aluminum chloride.

3. A method according to claim 1, wherein in step 1 the molar ratio of phenanthrene to formaldehyde is about 1 to 1 and that of phenanthrene to acid catalyst is about 1 to 2.

4. A method according to claim 1, wherein step 1 is carried out using glacial acetic acid as the solvent.

5. A method according to claim 1, wherein the molar ratio of reaction product to formaldehyde in step 3 is about 1 to 10.

6. A method according to claim 1, wherein the high molecular weight product is oxidized by use of a peroxy organic acid.

7. A method according to claim 1, wherein the polycarboxylated reaction product is dehydrated to form intra-anhydrides before it is reacted with the aromatic diamines.

8. A poly-(amide-imide) resin when made according to any one of the preceding claims.

* * * * *